(12) United States Patent
Wun

(10) Patent No.: US 6,291,427 B1
(45) Date of Patent: Sep. 18, 2001

(54) ANTICOAGULANT COMBINATION OF LACI AND SULFATED POLYSACCHARIDES

(75) Inventor: Tze-Chein Wun, St. Louis, MO (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 08/453,937

(22) Filed: May 30, 1995

Related U.S. Application Data

(63) Continuation-in-part of application No. 08/166,186, filed on Dec. 13, 1993, now abandoned, which is a continuation of application No. 07/573,083, filed on Aug. 27, 1990, now abandoned.

(51) Int. Cl.$^7$ ................................................. A61K 38/17
(52) U.S. Cl. ................................ 514/12; 514/21; 530/395
(58) Field of Search ........................ 514/12, 21; 530/395

(56) References Cited

U.S. PATENT DOCUMENTS 4,379,142    4/1983    Port et al. ............................ 424/101

FOREIGN PATENT DOCUMENTS

91/19514    12/1991    (WO) ............................ A61K/37/64

OTHER PUBLICATIONS

Wun, J. Biol. Chem. 263, 6001–6004 (1988).
Broze et al., Blood 71, 335–343 (988).
Broze & Miletich, Proc. Natl. Acad. Sci. 84, 1886–1890 (1987).
Rapapport, Blood 73, 359–365 (1989).
Goodman and Gilman's "The Pharmaceutical Bases of Therapeutics," Ch. 58, pp 1348–1353, 6th ed. 1980, section on "Heparin".
The Merck Index, No. 4571, 11th ed. 1989.
Girard et al., Science 248, 1421–1424 (1990).

*Primary Examiner*—Chhaya D. Sayala
(74) *Attorney, Agent, or Firm*—Scott J. Meyer

(57) ABSTRACT

There is disclosed herein a combination of lipoprotein-associated coagulation inhibition (LACI) and sulfated polysaccharides, e.g. heparin, which exerts a synergistic anticoagulant action in whole plasma.

6 Claims, 9 Drawing Sheets

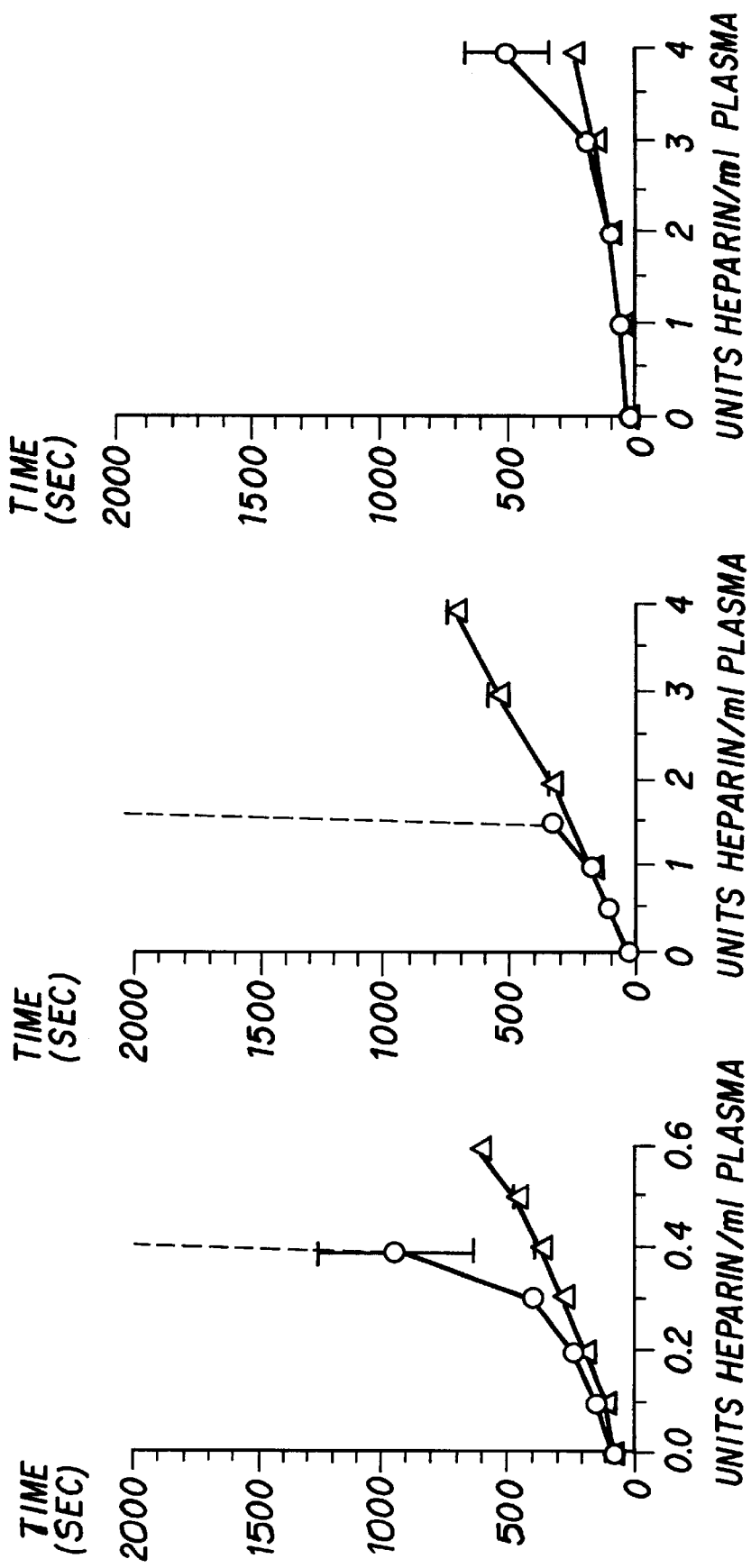

ANTICOAGULANT COMBINATION OF LACI AND SULFATED POLYSACCHARIDES

Figure 1:
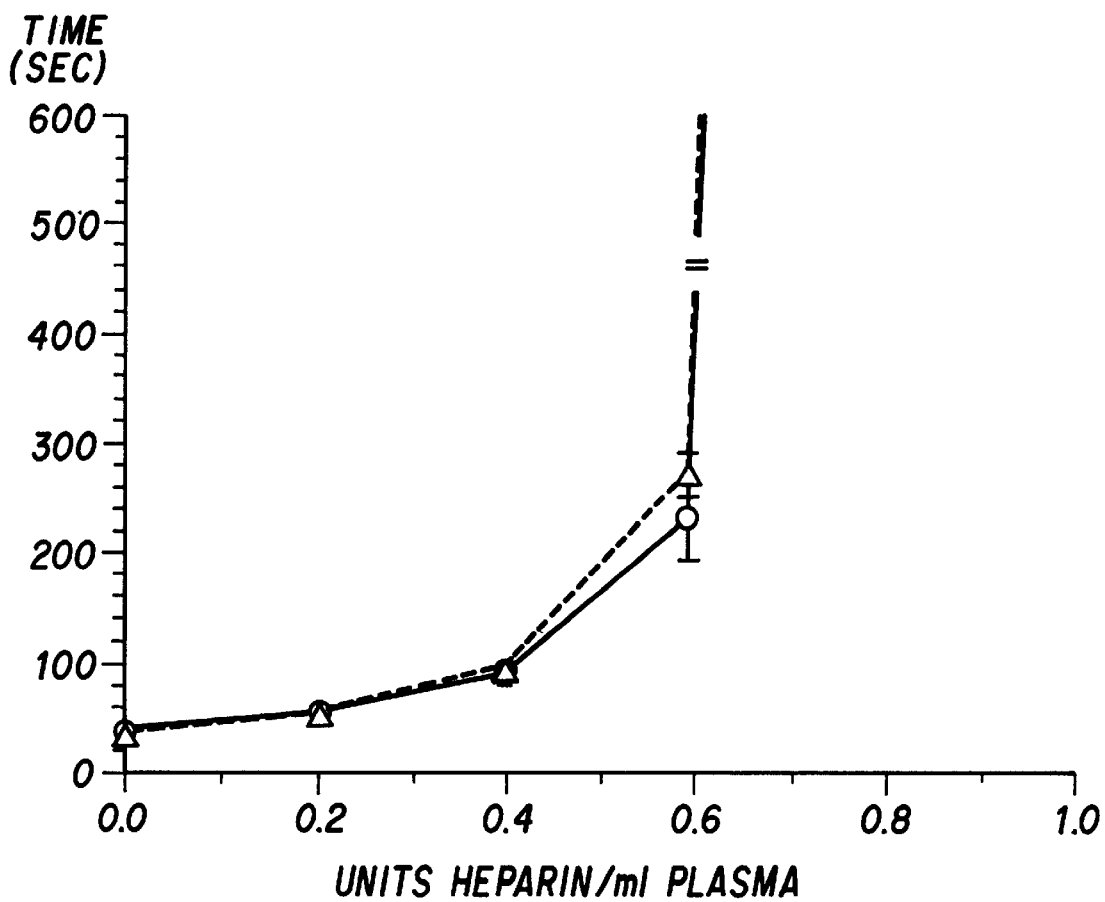

This is a C-I-P Appln. Ser. No. 08/166,186, filed Dec. 13, 1993 now abandoned, which is a continuation of Ser. No. 07/573,083, filed Aug. 27, 1990 both abandoned.

BACKGROUND OF THE INVENTION

This invention relates to an anticoagulant combination of LACI and sulfated polysaccharides and, more particularly, to a combination of LACI and heparin or similar such anticoagulant sulfated polysaccharides which exerts a synergistic anticoagulant action in whole plasma.

Blood clotting can be activated via the intrinsic or the extrinsic pathways. The intrinsic pathway begins with the contact phase which involves the interaction of factor XII, kallikrein, high molecular weight kininogen, a foreign surface and factor XI. The product of this reaction, factor $XI_a$, converts factor IX to factor $IX_a$, which subsequently hydrolyzes factor X to factor $X_a$ in the presence of activated factor VIII, phospholipid, and calcium. Alternatively, the extrinsic pathway is initiated when plasma factor $VII/VII_a$, binds to tissue factor (TF; thromboplastin) to form a complex which proteolytically activates factors IX and X. Once factor $X_a$ is formed, either via the intrinsic or the extrinsic pathway, it can bind factor $V_a$, phospholipid, and calcium to form the prothrombinase complex which converts prothrombin to thrombin. Ultimately, thrombin causes the fibrin clot to form.

Heparin has been widely used as an anticoagulant in clinical conditions. The anticoagulant effect of heparin is to a large extent a direct consequence of its catalytic action on the inhibition of thrombin by antithrombin III, and to a lesser extent its catalytic action on the inhibition by antithrombin III of other coagulation proteases including factors $XII_a$, $XI_a$, $IX_a$, $X_a$ and kallikrein (1–4). In the absence of heparin, antithrombin III does not inhibit factor $VII_a$ (5–8). In the presence of heparin, factor VII, was reported to be resistant to inhibition (6) or inhibited 50% by antithrombin III in 11 min (7), 75–90 min (8) or 6 hours (5). Thus the rate of factor VII, inhibition by antithrombin III is so slow that antithrombin III is unlikely a physiological regulator of the TF/factor VII pathway in the presence or the absence of heparin (9). In addition to the antithrombin III-dependent inhibition of proteases of the intrinsic pathway, heparin can also exert anticoagulant action by displacing factor $X_a$ and prothrombin from the prothrombinase complex in an antithrombin III-independent fashion (10, 11).

In the past few years evidence has accumulated that regulation of the extrinsic pathway may primarily involve a plasma-derived protein called lipoprotein-associated coagulation inhibitor (LACI) (12). This protein also has been referred to as extrinsic pathway inhibitor (EPI) (13), or tissue factor inhibitor (TFI) (14). The inhibitor is capable of complexing with factor $X_a$ directly, and inhibits TF activity by formation of an inert TF/factor $VII_a$/factor $X_a$/$Ca^{2+}$/inhibitor complex (12). Following the purification of apparently related inhibitor from Hep G2 hepatoma (14), the cDNA coding for the protein was subsequently cloned (15). Recently, expression of recombinant protein has generated large quantity of protein for in vitro and in vivo use.

The isolation of LACI from the conditioned media of Hep G2 cells, SK-Hep-1 cells, and Chang liver cells also is disclosed in co-pending application Ser. No. 07/77,366, filed Jul. 23, 1987, and the cloning of the cDNA coding for the LACI protein also is disclosed in co-pending application Ser. No. 07/123,753, filed Nov. 23, 1987, now allowed.

References cited herein by numbers in parentheses are listed hereinbelow.

BRIEF DESCRIPTION OF THE INVENTION

The present invention relates to a novel anticoagulant combination of lipoprotein-associated coagulation inhibitor (LACI) and sulfated polysaccharides. It has been surprisingly found that this combination exerts a synergistic anticoagulant action in whole plasma.

In a preferred embodiment of the invention, LACI and heparin cause a greatly enhanced anticoagulation compared to either LACI or heparin alone. Many related sulfated polysaccharides having known anticoagulant activity were also found to enhance the LACI-dependent inhibition of TF-induced clotting. By weight, the relative potencies of these compounds are in the following order: low molecular weight heparin (mean $M_r$=5,100)>unfractionated heparin>low molecular weight heparin (mean $M_r$=3,700) >pentosan polysulfate>dermatan sulfate>dextran sulfate>heparan sulfate.

Because of the unique mechanism and ability of LACI in the inhibition of TF-induced coagulation, LACI has been described heretofor as a potential therapeutic protein for the treatment/prevention of thrombotic diseases. The synergistic use of heparin and LACI in combination as described herein for therapeutic applications thus is highly attractive for the following reasons: first, heparin is widely available and may reduce the amount of LACI required for treatment by potentiating the LACI function; second, heparin and LACI in combination inhibit both the intrinsic and extrinsic pathways of coagulation; and third, the combination may be effective in clinical conditions where heparin alone is not sufficient, e.g. disseminated intravascular coagulation where TF may be generated in large amounts.

The dosages of the LACI and sulfated polysaccharides used for inhibiting coagulation preferably are small but effective amounts for producing a synergistic anticoagulation result. Use of from about 0.1 to about 4 units of heparin per ml of plasma in combination with from about 0.1 $\mu$g to about 5 $\mu$g of LACI per ml of plasma is preferred for the synergistic anticoagulant activity. Other sulfated polysaccharides can also be used in various amounts and proportions with LACI to produce synergistic anticoagulant effects. Use of the following amounts, respectively, of these other sulfated polysacharides with from about 0.1 to about 5 $\mu$g of LACI are preferred for synergistic anticoagulant activity:

0.2–2 $\mu$g/ml low molecular weight heparin (mean $M_r$=5, 100)

1–10 $\mu$g/ml low molecular weight heparin (mean $M_r$=3, 700), 4.5–45 $\mu$g/ml pentosan polysulfate, 34–340 $\mu$g/ml dermatan sulfate, 50–500 $\mu$g/ml dextran sulfate (mean $M_r$=6,000–8,000), and 100–1,000 $\mu$g/ml heparan sulfate.

As used herein, LACI is defined to mean lipoprotein-associated coagulation inhibitor as described by Wun et al., J. Biol. Chem. 263, 6001–6004 (1988). LACI can be isolated from various known sources, e.g., the conditioned media of cultured liver cells such as Hep G2 cells, SK hepatoma cells and Chang liver cells, or produced by recombinant DNA procedures. Although specific methods of isolation or production of LACI are described herein, it will be understood that the invention is not limited to any particular source of the LACI.

As used herein, one unit of heparin is defined to mean one U.S.P. (United States Pharmacopoeia) unit. The U.S.P. unit of heparin is that quantity which will prevent 1.0 ml of citrated sheep plasma from clotting for one hour after the addition of 0.2 ml of a 1:1000 $CaCl_2$ solution. Heparin is generally obtained by isolation from mammalian tissues containing mast cells such as the liver and lung. As used herein, the term "heparin" also is meant to include the pharmaceutically acceptable water soluble salts thereof, e.g., the sodium salt. Suitable examples of commercially available heparin sodium products are Lipo-Hepins® (Riker Laboratories), Liquaemin® Sodium (Organon), and Panheprin® (Abbott Laboratories).

DETAILED DESCRIPTION OF THE INVENTION

While the specification concludes with claims particularly pointing out and distinctly claiming the subject matter regarded as forming the present invention, it is believed that the invention will be better understood from the following preferred embodiments taken in conjunction with the accompanying drawings which are graphical representations in which:

FIG. 1 shows the effect of heparin on the activated partial thromboplastin time (APTT) of a normal plasma and the same plasma depleted of endogenous LACI. A frozen plasma was thawed and used without pretreatment or used after immunoadsorption with an anti-LACI-Ig Sepharose 4B to deplete the endogenous LACI. The plasmas were supplemented with various concentrations of heparin and the APTT was determined as described in METHODS, below. Original plasma, -○-; LACI-depleted plasma, -Δ-. The extrapolations beyond 0.6 units heparin/ml plasma were based on the results that both plasmas remained unclotted for more than 1 h at 0.8 units heparin/ml plasma.

FIG. 2 shows the effect of heparin on the prothrombin time (PT) of a normal plasma and a LACI-depleted plasma at various tissue factor (TF) concentrations. The plasmas used were either untreated (○) or depleted of endogenous LACI antigen (Δ) by immunoadsorption as described in METHODS, below. TF reagent was diluted 1:1000 (panel A), 1:100 (panel B), or 1:10 (panel C) for the determination of PT. The dashed lines in panels A and B were extrapolations based on the results that the plasmas remained unclotted for more than 1 h at 0.5 (panel A) and 2 (panel B) units heparin/ml plasma, respectively.

FIG. 3 shows the effect of exogenously added LACI on the PT of a plasma induced to clot by various concentrations of TF. Panel A, TF reagent was diluted 1:10,000 (-□-), 1:1000 (○) and 1:100 (-●-) for the determination of PT. Panel B, TF reagent was used at 1:10 dilution.

FIG. 4 shows a test of synergy between heparin and LACI in prolonging the PT of a LACI-depleted plasma. (A) Effect of LACI, heparin, and a combination of LACI and heparin on the PT of a LACI-depleted plasma. A LACI-depleted plasma was supplemented with LACI (-x-), heparin (-□-), or a combination of LACI and heparin (-▲-), and their PTs were determined as described in the METHODS, below, using 90 µl of 1:100 dilution of the TF reagent. (B) Isobolar analysis of the LACI/heparin interaction. Concentrations of LACI alone, heparin alone and LACI/heparin in combination which give the same PTs (isoeffective clotting times of 80, 100, 120, 140, 160, 180 and 200 sec) were determined from the curves in panel (A). Da and Db are the concentrations of LACI and heparin separately that are isoeffective with the LACI/heparin combination at concentrations of da and db, respectively. The values of da/Da+db/Db reflect whether the two agents interact. A value of=1 suggests zero interaction; a value of >1 indicates antagonism; and a value of <1 shows synergy.

Figure 5:
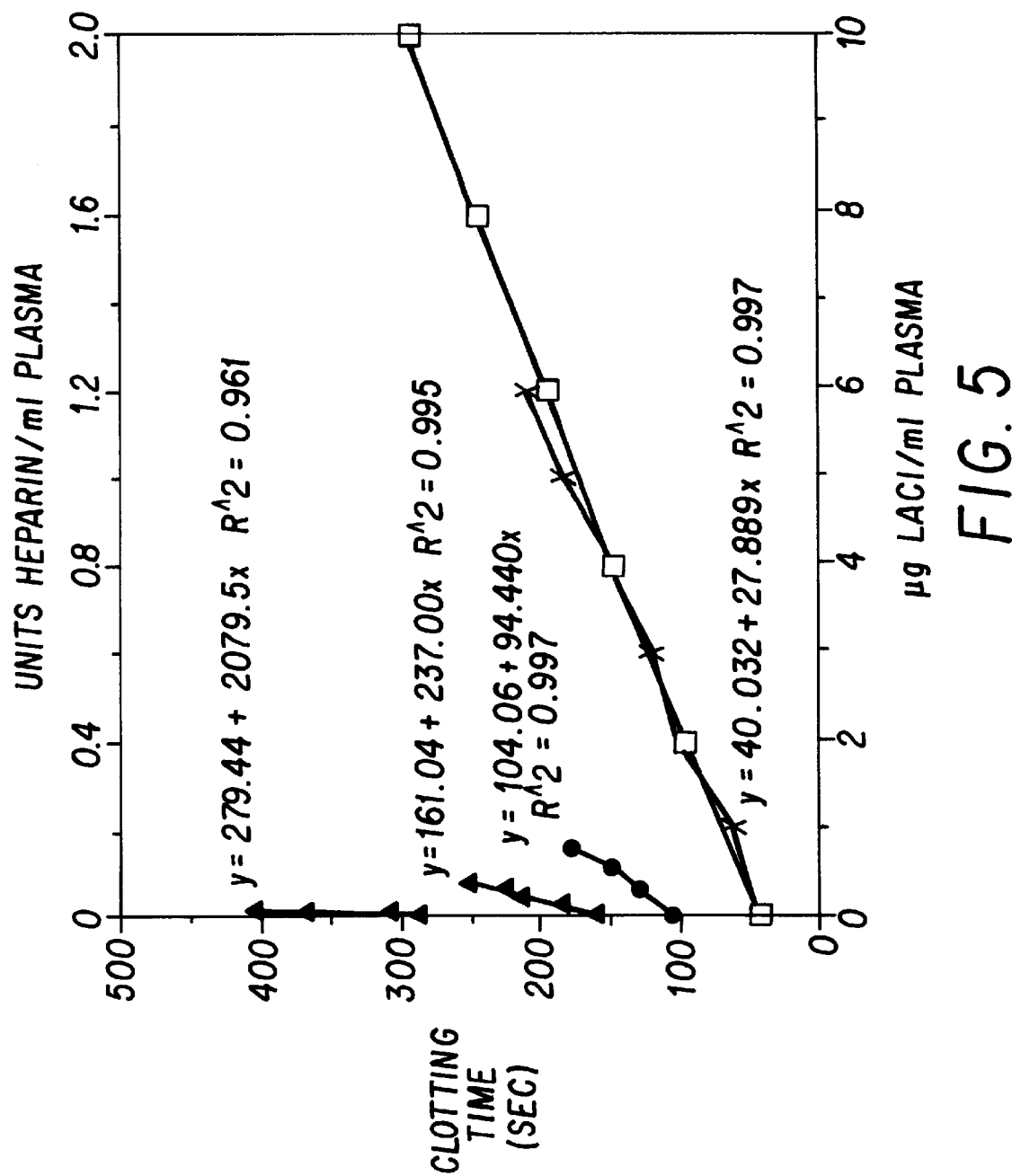

FIG. 5 shows the effect of LACI, heparin, and the combination of LACI and heparin on the PT of a plasma depleted of endogenous LACI. Plasma was depleted of endogenous LACI by immunoadsorption on an anti-LACI-Ig Sepharose 4B column. PT was determined as described in the METHODS, below, using 90 µl of 1:100 dilution of the TF reagent. LACI-depleted plasma was supplemented with various amounts of LACI (-x-), heparin (-□-), and LACI in combination with 0.5 (-●-), 1.0 (-▲-), and 2.0 (-Δ-) units heparin per ml plasma, respectively. Equations and correlation coefficients from linear regression analysis are shown.

Figure 6:
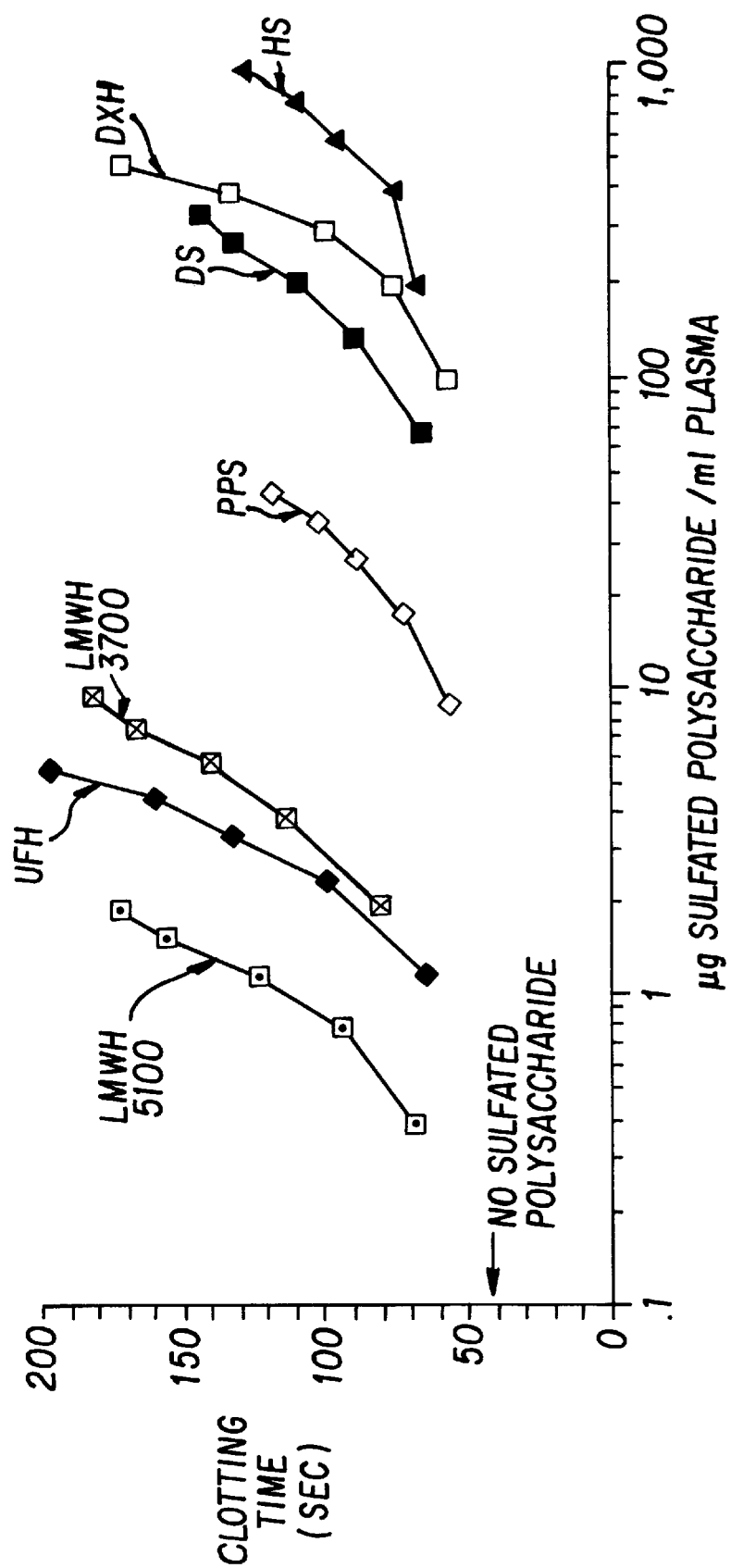
Figure 7A:
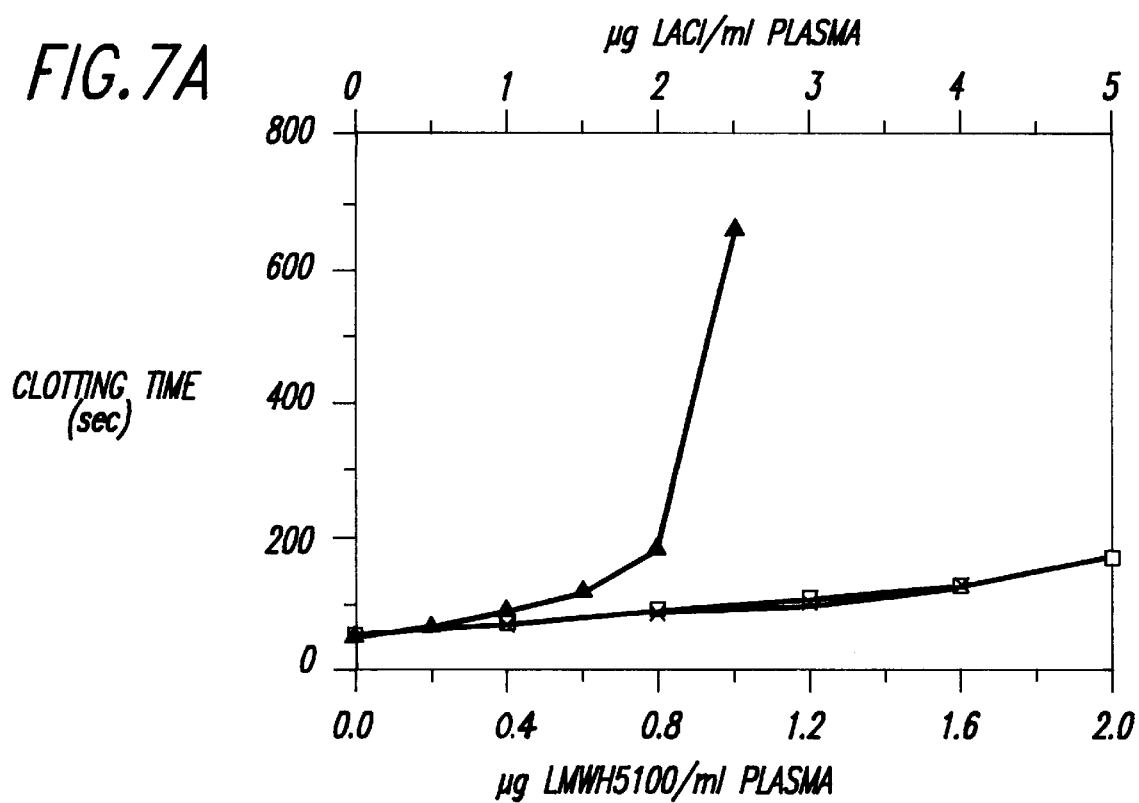
Figure 7B:
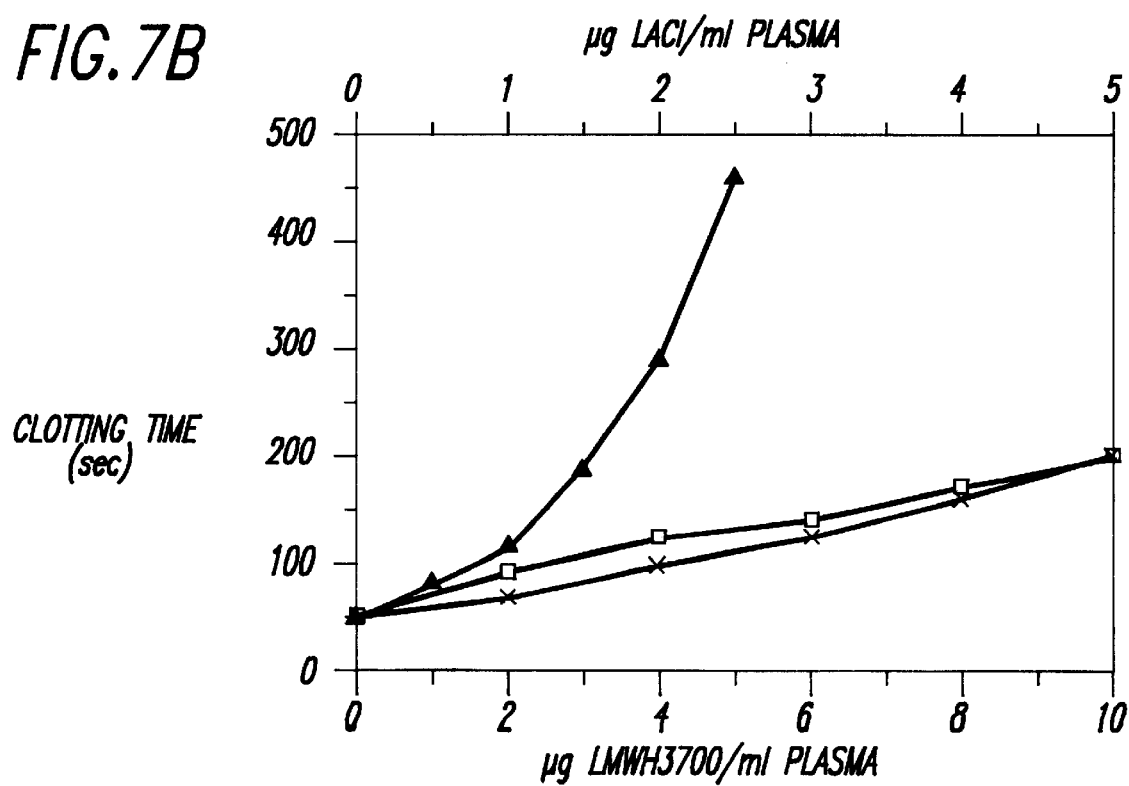
Figure 7C:
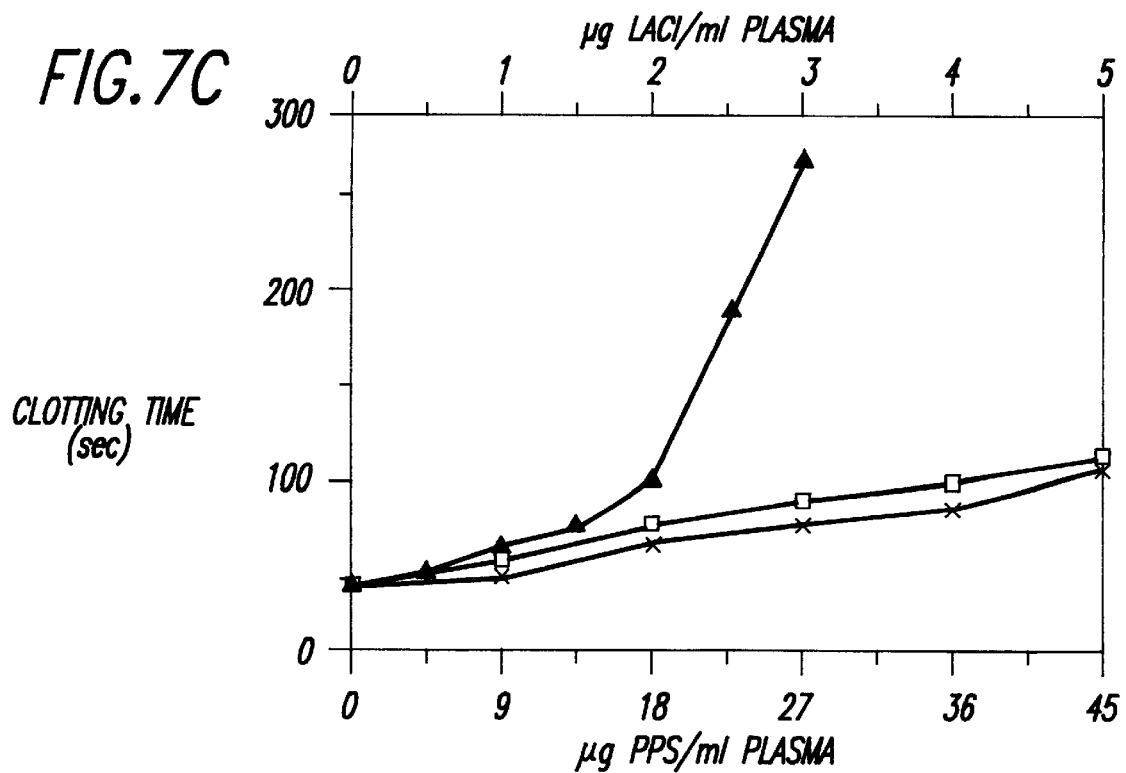
Figure 7D:
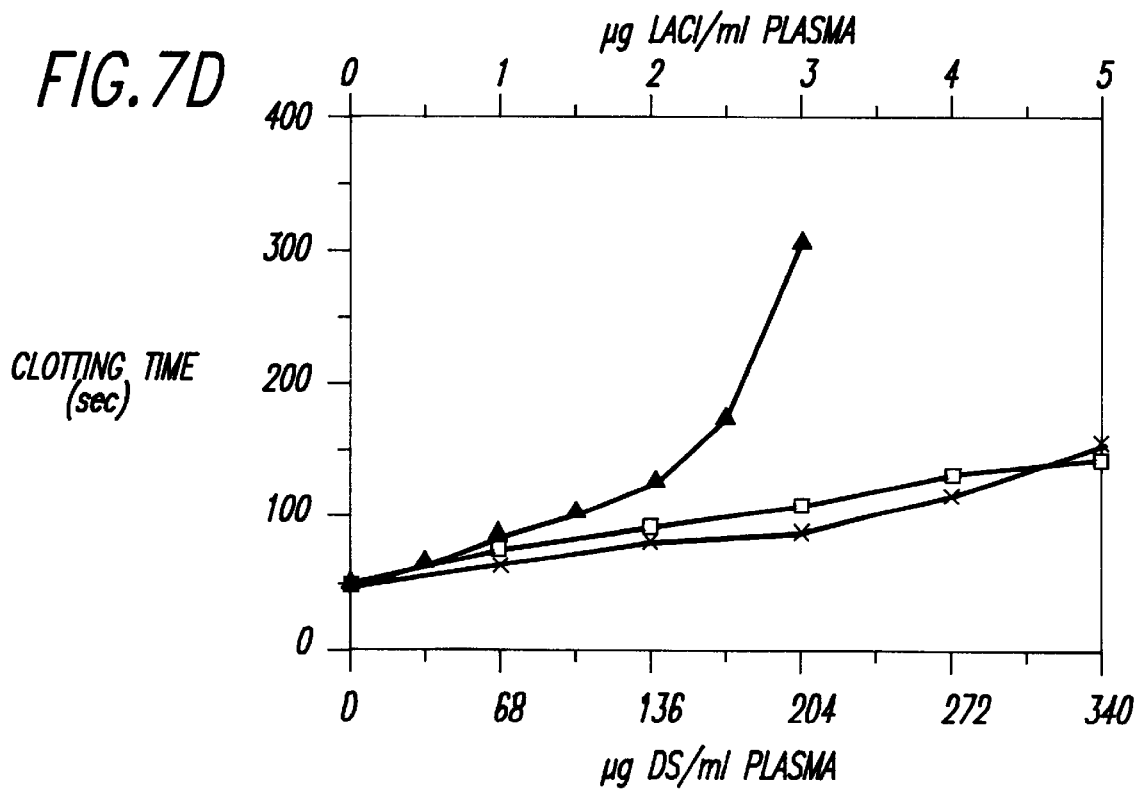
Figure 7E:
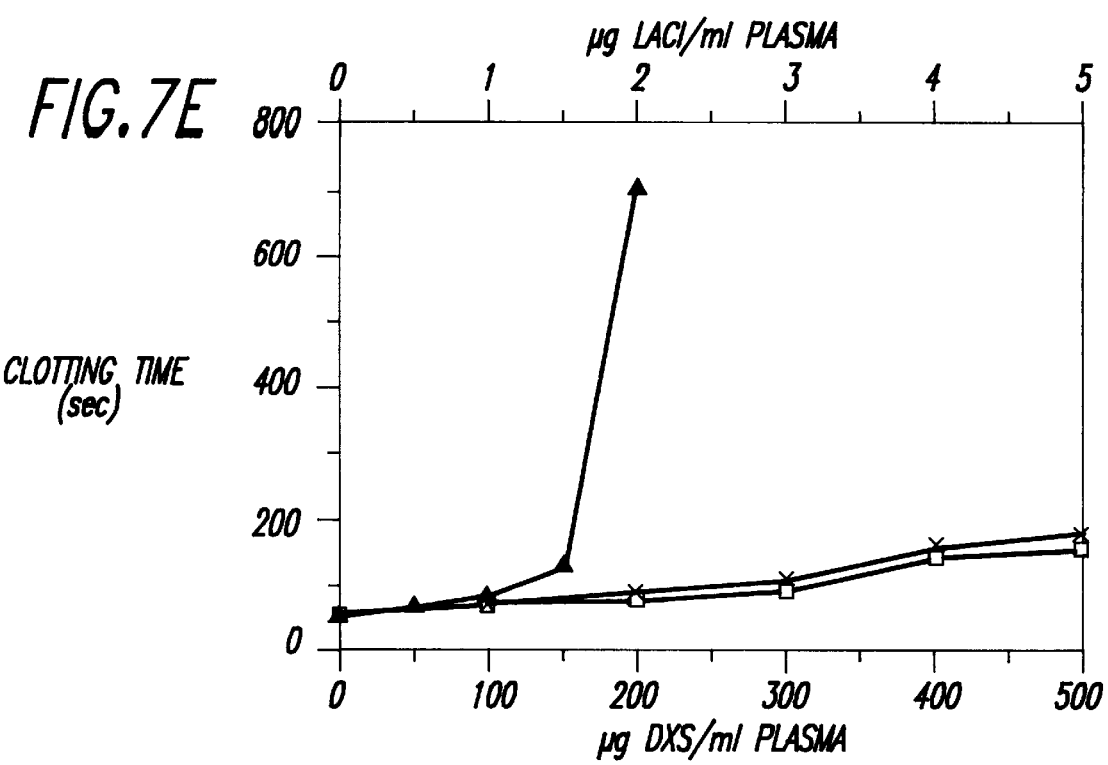
Figure 7F:
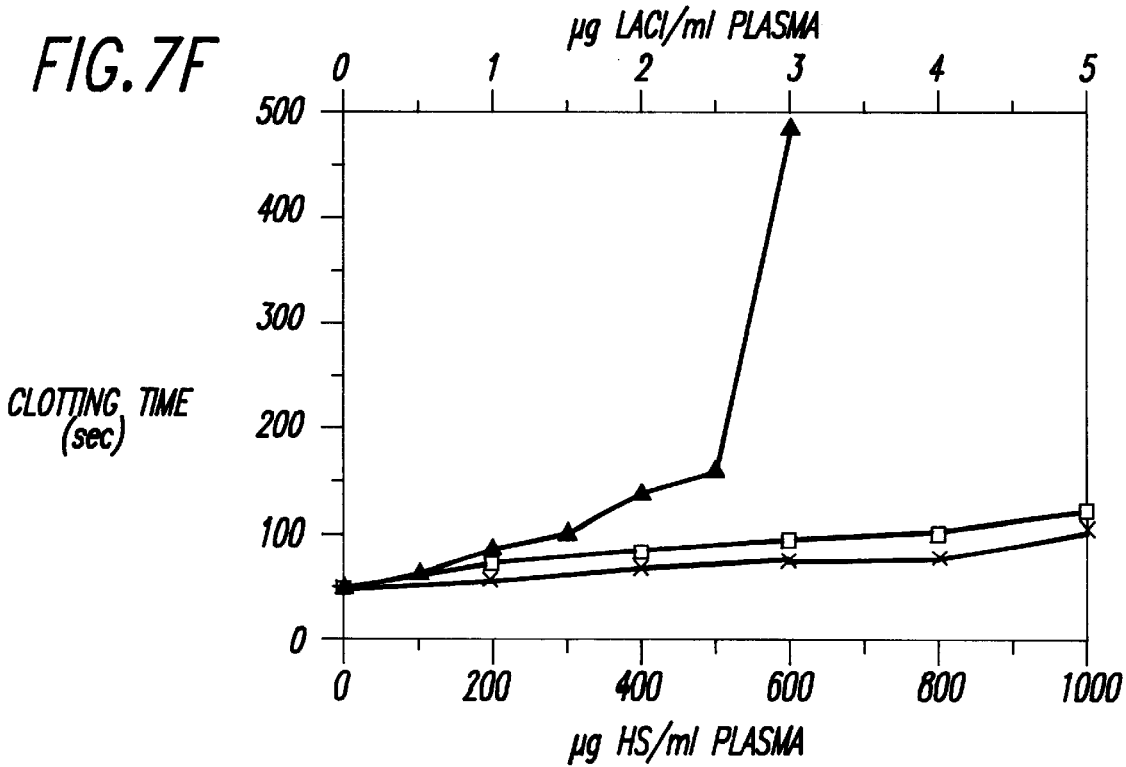

FIG. 6 shows the effect of sulfated polysaccharides on the PT of normal plasma. PT was determined as described in METHODS, below, using 90 µl of 1:100 dilution of the TF reagent, 10 µl of sulfated polysaccharides, 100 µl of a pooled plasma, and 100 µl of 25 mM $CaCl_2$. The sulfated polysaccharides used are LMWH5100 (low molecular weight heparin, mean $M_r$=5100); UFH (unfractionated heparin); LMWH3700 (low molecular weight heparin, mean $M_r$=3700); PPS (pentosan polysulfate); DS (dermatan sulfate); DXS (dextran sulfate, mean $M_r$=6000–8000); and HS (heparan sulfate).

FIG. 7 shows the effect of sulfated polysaccharides, LACI, and the combination of sulfated polysaccharides/LACI on the PT of a pooled plasma. PT was determined as described in METHODS, below, using 90 µl of 1:100 dilution of the TF reagent, 10 µl of sulfated polysaccharide, LACI, or a combination of the two at the concentrations indicated, 100 µl of a pooled plasma, and 100 µl of 25 mM $CaCl_2$. The compounds used are the same as those in FIG. 6. LACI alone (-x-); sulfated polysaccharide alone (-□-); a combination of LACI and sulfated polysaccharide, (-▲-).

The novel anticoagulant combination of LACI and sulfate polysaccharides is further illustrated herein in detail by a combination of recombinant LACI (rLACI) expressed in mouse C127 cells and heparin and related sulfated polysaccharides.

The LACI employed herein is a known plasma-derived inhibitor that inhibits the tissue factor (TF)/factor VII-induced coagulation in a factor Xa-dependent manner. The roles of the endogenous plasma LACI and the exogenously added LACI and heparin in the regulation of coagulation initiated by the intrinsic and extrinsic pathways were tested by employing an activated partial thromboplastin time (APTT) assay and a modified prothrombin time (PT) assay. Such assays are conventional in the field of hematology for measuring the effect of heparin on blood clotting times. See, e.g., U.S. Pat. No. 3,486,981. The LACI-depleted plasma and the normal plasma have identical APTTs and similar prolongations of the APTT in response to heparin; and both are fully anticoagulated (arbitrarily defined as clotting times of more than 1 h.) at similar concentrations of heparin. These results indicate that heparin is a very effective anticoagulant when coagulation is initiated by the intrinsic pathway and that endogenous LACI is not significantly involved in the regulation of this pathway. The PT of normal plasma is only marginally longer than that of LACI-depleted plasma in the absence of heparin, suggesting that endogenous plasma LACI has a very limited capacity to inhibit the TF-induced clotting. However, in the presence of heparin, the PTs of LACI-depleted plasma and PT normal plasma are very different. Prolongation of the PT occurred only moderately and linearly with increasing concentrations of heparin in LACI-depleted plasma; in contrast, normal plasma showed a greater extent of PT prolongation in response to the heparin and the plasma became fully anticoagulated at a certain threshold concentration of heparin. These results suggest that LACI serves as a cofactor for heparin and thus greatly enhances the inhibition of TF-induced clotting. LACI-depleted plasma was supplemented with purified recombinant LACI, heparin, or a combination of the two and their effects on the TF-induced clotting were tested. It was unexpectedly found that LACI and heparin in combination caused a greatly enhanced anticoagulation compared to LACI or heparin alone. Many sulfated polysaccharides were also found to enhance the LACI-dependent inhibition of TF-induced clotting. The effective ranges of these compounds are: low molecular weight heparin (mean $M_r$=5, 100), at 0.2–2 μg/ml; unfractionated heparin, at 0.1–4 units/ml; low molecular weight heparin (mean $M_r$=3,700), at 1–10 μg/ml, pentosan polysulfate, at 4.5–45 μg/ml; dermatan sulfate, at 34–340 μg/ml, dextran sulfate, at 50–500 μg/ml; and heparan sulfate, at 100–1000 μg/ml. Based on the above results, it is concluded that LACI is a cofactor for heparin in the TF-induced clotting and that LACI and sulfated polysaccharides exert synergistic anticoagulant action in whole plasma.

The following examples will further illustrate the invention although it will be understood that the invention is not limited to these specific examples or the details therein.

EXAMPLES

Materials

Rabbit brain thromboplastin (tissue factor, TF) was obtained from Ortho Diagnostic. Dade's activated cephaloplastin reagent for the determination of activated partial thromboplastin time (APTT) was purchased from American Scientific Product. Unfractionated heparin (UFH, lot 038078) was obtained from Elkin-Sinn Inc. Low molecular weight heparins (LMWH) with mean molecular weight of 5100 and 3700 were from Calbiochem. Pentosan polysulfate (PS, #P8275), bovine mucosa dermatan sulfate (DS, #C2413), and bovine intestinal mucosa heparan sulfate (HS, #H7641) were from Sigma. Dextran sulfate (DXS, mean $M_r$=7,000–8,000) was supplied by ICN Biochemicals. Human plasma was provided by American Red Cross (St. Louis). Four units of plasma were pooled and stored frozen in aliquots at −80° C. until use. Bovine factor $X_a$, and Spectrozyme $X_a$ were obtained from American Diagnostica.

Methods
Expression and Purification of rLACI rLACI was expressed in mouse C127 cell using a bovine papilloma virus vector and the rLACI-producing cell line was grown in cell factory for harvesting of conditioned medium as follows:

The bovine papilloma virus-based vector, pMON1123, which consists of the entire bovine papilloma virus genome cloned in the pBR322 derivative of pML2, was used to express LACI. This vector uses the mouse metallothionine I promoter and the SV40 Late poly A addition site to direct the expression of proteins encoded by DNA fragments inserted into a unique BamHI site. The use of recombinat DNA processes utilizating a papilloma virus DNA as a vector for the replication and expression of exogenous genes in eukaryotic cells is conventional practice as can be seen from U.S. Pat. No. 4,419,446. For the expression of LACI cDNA, pMON1123 was digested with BamHI and the 5' overhanging ends were filled in with Klenow fragment (Boehringer Mannheim, Indianapolis, Ind.) and deoxynucleotides (dNTPs). Similarly, the LACI cDNA was isolated as an EcoRI fragment and the ends were rendered blunt by Klenow fill-in. The LACI fragment was ligated into pMON1123 to yield the plasmid pMON1456. Mouse c127 cells were grown and co-transfected with pMON1456 and pSVneo by procedure as previously described by Ramabhadran et al., *Proc. Natl. Acad. sci. U.S.A.* 81, 6701 (1984). Following selection with G418 antibiotic (Geneticin), resistant colonies were picked and seeded into 24-well plates. Conditioned media from each well were then assayed for recombinant LACI (rLACI) expression by an enzyme-linked immunosorbent assay (ELISA). One clone, 1455–15, expressing approximately 1 to 2 μg LACI/$10^6$ cell24 h, was expanded for isolation of rLACI.

The rLACI-producing cell line 1455–15 was cultured in Dulbecco's Modified Eagle's Medium containing 10% fetal bovine serum. The cells were grown in 150 cm$^2$ flasks to conf luency. Each flask was then trypsinized and used to seed one 850 cm$^2$ roller bottle. After confluency, the cells from each roller bottle were used to seed one 10-chamber cell factory (6,000 cm$^2$; GIBCO Laboratories, Grand Island, N.Y.). On reaching confluency, the cells were washed with phosphate-buffered saline and incubated in a serum-free medium consisting of Dulbecco's Modified Eagle's Medium, supplemented with 0.2 μg/mL menadione, 2.5 mmol/L sodium butyrate, and 50 U/mL aprotinin. The serum-free conditioned medium was collected every 2 days and replaced with fresh medium.

The serum-free conditioned medium was adjusted to 50 mM $(NH_4)_2SO_4$, filtered through a 0.2 μfilter and concentrated 30-fold using an Amicon YM30 radial cartridge concentrator. The concentrate was subjected to ammonium sulfate precipitation. Protein precipitated between 23–90% saturation of ammonium sulfate were collected and dialyzed against phosphate buffered saline containing 20 mM $Na_2SO_4$. Triton X-100 detergent was added to a final concentration of 0.05% and the solution was clarified by centrifugation at 40,000×g for 1 h. The supernatant was chromatographed on an anhydrotrypsin-Sepharose 4B column (12 ml gel, prepared according to the method described in ref. 17) equilibrated in phosphate buffered saline containing 20 mM $Na_2SO_4$, 0.05% Triton X-100 (buffer A). The column was washed with 80 ml of buffer A and 80 ml of the same buffer without Triton X-100. The bound protein was eluted with 1.5 M NaSCN in three column volumes. The eluted protein was concentrated and dialyzed against a solution containing 0.15 M NaCl and 20 mM $Na_2SO_4$. The recovery of LACI was about 60%. The freshly prepared anhydrotrypsin-Sepharose 4B column had a capacity of about 0.6 mg LACI/ml gel. Upon repeated use, the capacity decreased to about 0.2 mg/ml gel. Sodium dodecyl sulfate polyacrylamide gel electrophoresis (SDS-PAGE) of the eluted protein shows a major band of $M_r$~38,000 corresponding to LACI with traces of high molecular weight contaminants. The contaminants were removed by adsorption with phenyl Sepharose 4B.

Characterization of Purified rLACI

The isolated protein is substantially pure LACI by the following criteria: (a) SDS-PAGE shows essentially a single band; (b) amino acid analysis and protein sequencing match the composition and sequence deduced from the cDNA sequence of LACI; and (c) the stoichiometry of the inhibition of factor $X_a$ in an amidolytic substrate assay is approximately 1:1 (see below).

The concentration of LACI was quantitated by amino acid analysis. The active site concentration of factor $X_a$ was measured by titration with p-nitrophenyl-p'-guanidinobenzoate according to Chase and Shaw (16). The amidolytic activity of factor $X_a$ and the anti-factor $X_a$ activity of LACI were determined as follows: Ten µl of bovine factor $X_a$ (0.084 pmol active molecule) was mixed with 10 µl of TBB buffer (Tris-buffered saline containing 5 mg/ml bovine serum albumin and 2.5 mg/ml bovine gamma globulin) or 10 µl of properly diluted LACI in TBB buffer in a disposable cuvette for 5 min at room temperature. After addition of 0.22 ml of an assay buffer (0.1 M Tris/HCl, pH 8.4, 0.5% Triton X-100) and 10 µl of Spectrozyme $X_a$ (12.5 mM), the rate of the absorbance change at 405 nm was measured at 37° C. The control gave an absorbance change of 0.0233 per min. per 0.1 pmol of active factor $X_a$ at 405 nm. In the reaction mixture containing LACI, the anti-$X_a$ activity was calculated based on the decrease of factor $X_a$ activity compared with that of the control. Using the assays described above, 2.6 ng of purified LACI (based on amino acid analysis; equivalent to 0.068 pmol assuming $M_r$=38,000) was found to inhibit 0.066 pmol, of active factor $X_a$. Thus, the stoichiometry of the interaction between LACI and factor $X_a$ appears to be 1:1.

Activated Partial Thromboplastin Time (APTT)

Dade's activated cephaloplastin reagent was used to determine the APTT of plasma using a Fibrometer clot timing instrument. Ninety µl of plasma was mixed with 10 µl of sulfated polysaccharide or control buffer and 100 µl of activated cephaloplastin reagent for exactly 2 min. at 37°. A calcium solution (100 µl of 25 mM $CaCl_2$) was added to the mixture and the time to clotting was recorded. The assay was observed for up to 1 hour. For practical purposes, the plasma is arbitrarily referred to as "fully anticoagulated" when clotting does not occur in 1 h.

Prothrombin Time (PT)

Rabbit brain thromboplastin (TF, Ortho Diagnostic) was diluted 1:10, 1:100, 1:1000, or 1:10,000 in a saline solution containing 1 mg/ml bovine serum albumin for the determination of PT. One hundred µl of plasma was mixed with 10 µl of control buffer, LACI solution, or sulfated polysaccharide solution and 90 µl of a diluted TF in the well of the Fibrometer at 37° C. for 2 min. One hundred µl of 25 mM $CaCl_2$ was added and the time to clotting was determined. The concentrations of the sulfated polysaccharides and LACI refer to the amounts of these compounds per ml of undiluted plasma (not the concentration of the final mixture). The PTs reported here are the average of 2–8 determinations depending on the length of the clotting time. When the clotting time was short (<100 sec), the variations between determinations are small and 2–3 assays were made and averaged for each data point. When the clotting time was long (>100 sec) and the variations were larger due to the use of dilute TF or high concentrations of LACI and sulfated polysaccharides, 4–8 determinations were made and averaged for each data point. The assay was observed for up to 1 hour. The plasma is referred to as "fully anticoagulated" when clotting does not occur in 1 h.

Antiserum, Anti-LACI-Ig, and Anti-LACI-Ig Sepharose 4B

Two New Zealand white rabbits were each immunized by intradermal injection with a homogenate containing 1 ml of Freund's complete adjuvant and 1 ml of purified LACI (200 µg of LACI protein). One month later the rabbits were each boosted with a homogenate containing 1 ml of freund's incomplete adjuvant and 1 ml of the purified LACI (100 µg of LACI protein). Antiserum was collected each week thereafter. Booster injection was performed monthly until the rabbits were exsanguinated after 3 months. Anti-LACI-Ig was isolated from the antiserum by chromatography on protein A-Sepharose 4B column. The isolated anti-LACI-Ig was coupled to cyanogen bromide-activated Sepharose 4B at a concentration of 10 mg of Ig/ml gel by Pharmacia's recommended procedure.

Preparation of LACI-depleted Plasma

Pooled frozen plasma (100 ml) was thawed and passed through an anti-LACI-Ig Sepharose 4B column (3 ml of gel containing ~15 mg of bound Ig) 5 times to deplete the endogenous LACI antigen. The immuno-adsorbed plasma was essentially depleted of endogenous LACI since an immunoassay (sensitivity of ~1 ng/ml) did not detect any LACI antigen.

RESULTS

Effect of Heparin on Intrinsic Coagulation

In the APTT assay, the contact phase proteins are activated which leads to the initiation of the intrinsic coagulation cascade. FIG. 1 shows the effect of heparin on the APTT of normal plasma and the same plasma depleted of endogenous LACI. A moderate prolongation of clotting time (up to 5-fold) was observed at heparin concentrations of 0 to 0.6 units/ml plasma. At 0.8 units heparin/ml, the plasma remained unclotted for more than 1 hour (arbitrarily defined as "fully anticoagulated"). There was no significant difference in APTT in normal plasma and the LACI-depleted plasma, suggesting that endogenous plasma LACI does not play a significant role in the regulation of the intrinsic coagulation in the presence or absence of heparin.

The Role of Endoaenous Plasma LACI in the Regulation of Extrinsic Coagulation

Normal plasmas were pre-incubated with anti-LACI-Ig or normal rabbit Ig and their PTs were measured to determine the role of endogenous plasma LACI in the regulation of extrinsic coagulation. As shown in Table 1, the PTs were shorter for the plasma treated with anti-LACI-Ig than that with normal Ig. However, the difference between the antibody treated plasma and the control were small at 1:10, 1:100, and 1:1,000 dilutions of TF. A moderate difference in the PTs was observed at 1:10,000 dilution of TF. Similar results were obtained using untreated plasma and plasma depleted of endogenous LACI by immunoadsorption with anti-LACI-Ig Sepharose 4B. These results suggest that the capacity and/or the ability of the endogenous LACI to inhibit TF-induced coagulation is rather small under these conditions.

Effect of Heparin on Extrinsic Coagulation

The effect of heparin on PTs of normal plasma and the same plasma depleted of endogenous LACI were measured using various concentrations of TF. FIG. 2(A) shows the results using 1:1,000 dilution of TF (PT=77 sec for the control without heparin). In the LACI-depleted plasma (Δ), increasing concentrations of heparin (0–0.6 units/ml plasma) progressively prolonged the PT in essentially a linear fashion. In plasma containing endogenous LACI (○), the heparin response was sigmoidal. At 0.1–0.2 units heparin/ml plasma, PT was the same or marginally longer than those in the LACI-depleted plasma. At 0.3 and 0.4 units heparin/ml plasma, PTs were 1.5- and 2.6-fold longer than those in the LACI-depleted plasma. At 0.5 units heparin/ml plasma, the plasma became "fully anticoagulated".

FIG. 2(B) shows the result using 1:100 dilution of TF (PT=41 sec for the control without heparin). In LACI-depleted plasma (Δ), the PT also linearly increased with increasing heparin concentration, but it required about 6 fold higher concentration of heparin to achieve the same PTs as those in FIG. 2(A). In plasma containing endogenous LACI (○), the heparin response was also sigmoidal, but the threshold concentration of heparin required to achieve "fully anticoagulated" state occurred at a concentration greater than 1.5 units heparin/ml plasma.

FIG. 2(C) shows a similar test using a 1:10 dilution of TF (PT=24 sec for the control without heparin). In the LACI-depleted plasma (Δ), heparin-induced prolongations of PT were much less than those in FIGS. 2(A) and (B). In the LACI-containing plasma, the PT remained less than 500 sec up to 4 units heparin/ml plasma.

The above results taken together suggest that several mechanisms may be involved in the regulation of the extrinsic coagulation. First, heparin can prolong TF-induced clotting moderately in the absence of endogenous LACI; second, endogenous plasma LACI possesses a weak anti-clotting effect against TF-induced clotting in the absence of heparin; and third, beyond a certain threshold concentration, heparin dramatically enhances the inhibition of TF-induced clotting in the presence of plasma LACI, suggesting that LACI serves as a cofactor for heparin in the inhibition reaction.

Effect of Exogenously added LACI on the PT of Normal Plasma

Figure 3A:
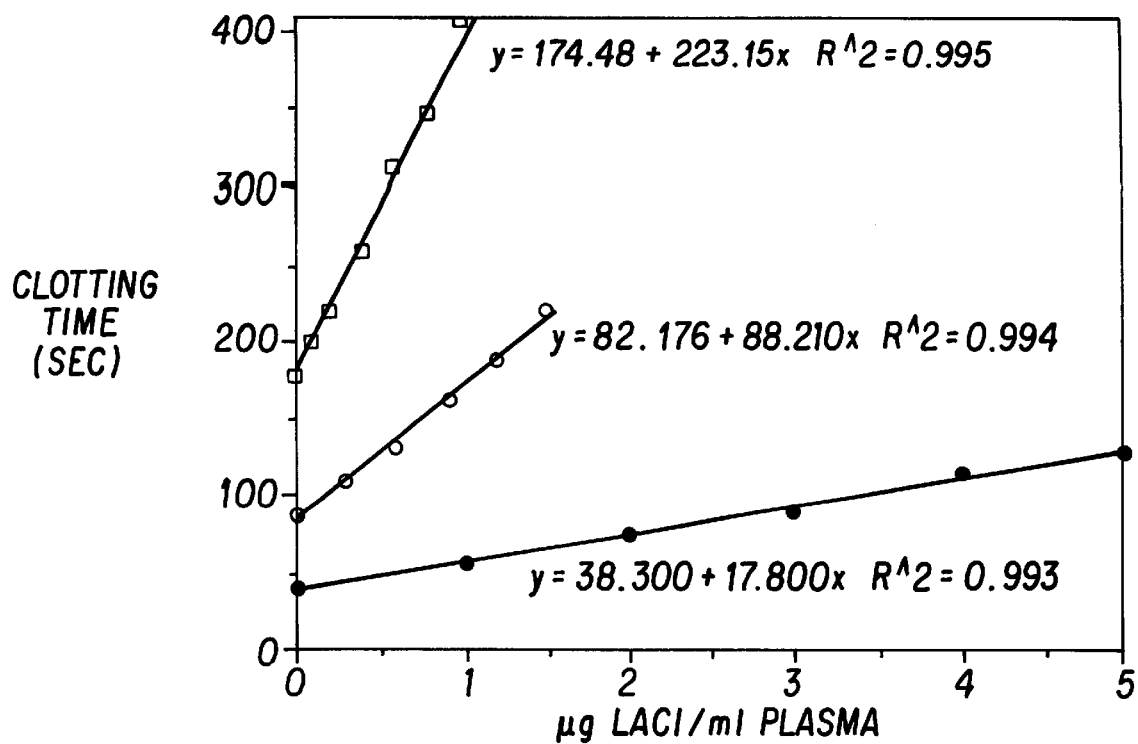
Figure 3B:
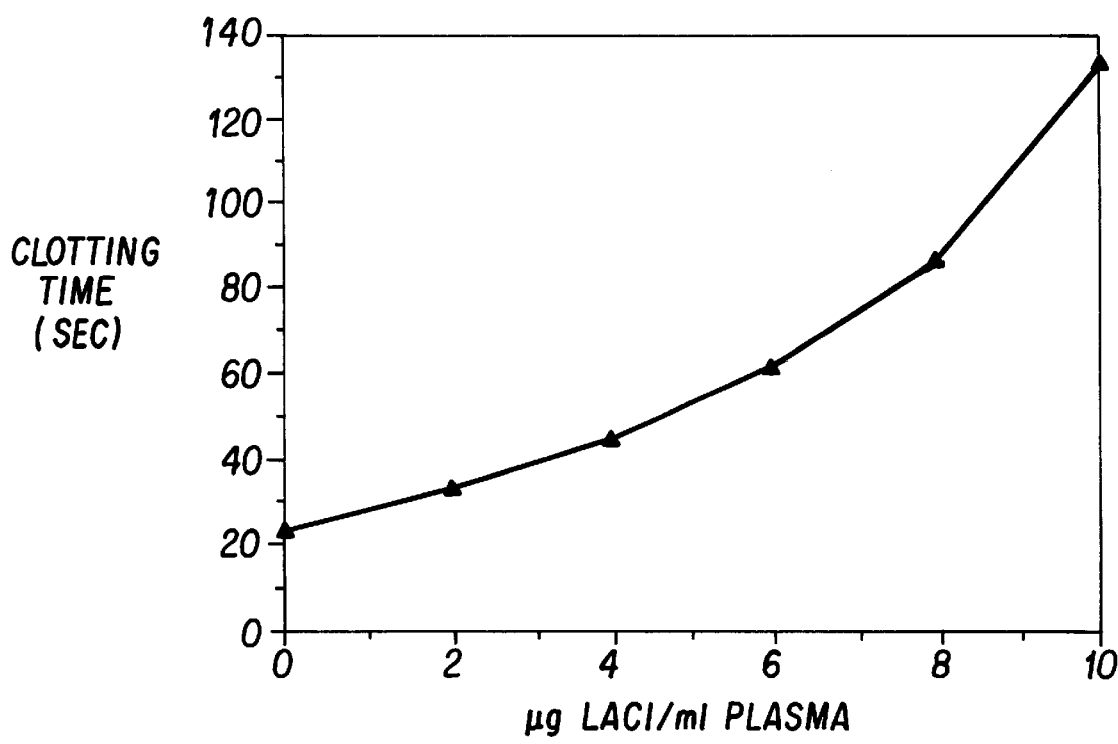

The tests described above are restricted to plasma containing or depleted of endogenous LACI. The results suggest that endogenous plasma LACI may play an important role in the inhibition of TF-induced clotting when the amount of TF is small, but it may be inadequate when the amount of TF is large. To extend the range of control to conditions where endogenous LACI are inadequate, exogenous LACI was added to normal plasma to examine its effect on the PT. FIG. 3(A) shows that using a wide range of constant concentrations of TF (1:10,000, 1:1,000, and 1:100 dilutions of TF), the PTs are linearly related to the concentration of the exogenous LACI added to the plasma. The concentration of LACI required for prolongation of the PT increases with increasing concentration of TF used, and this is reflected in the slope of the PT-LACI concentration response curves. At a higher concentration of TF used (1:10 dilution of TF), the PT-LACI concentration response curve is not linear as shown in FIG. 3(B).

Synergistic Anticoagulant Action of LACI and Heparin

Figure 4A:
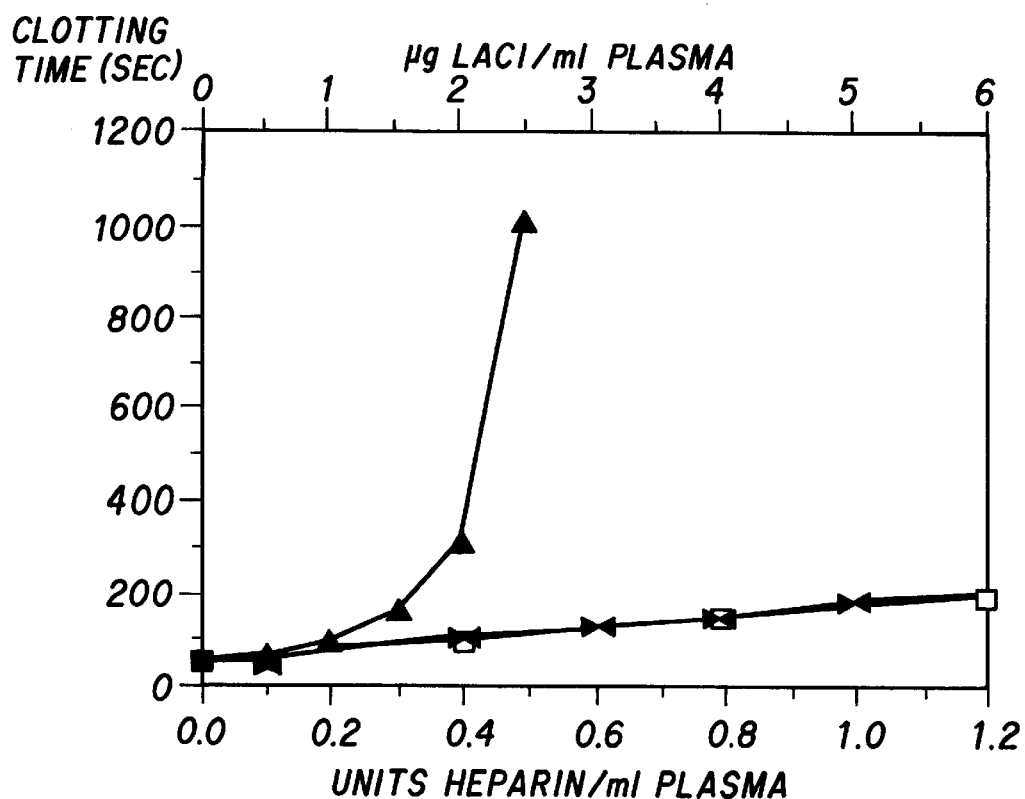

The above tests demonstrate that addition of heparin or LACI separately to plasma produces dose-dependent inhibition of TF-induced clotting (FIGS. 2 and 3). In addition, heparin appears to potentiate the inhibition of TF-induced clotting by endogenous LACI (FIG. 2). To quantitate the extent of potentiation, a LACI-depleted plasma was supplemented with heparin, purified LACI or a combination of both to compare their anticoagulant effects. FIG. 4(A) shows the relationship of the PT to the concentrations of exogenously added heparin and LACI. Prolongation of the PT with increasing concentrations of heparin (□) or LACI (x) alone are linear. When heparin and LACI are simultaneously present in plasma (▲), the total effect on the clotting time varies with the concentration of the compounds used. At low concentrations (e.g. <0.2 units heparin/ml plus <1 μg LACI/ml), the clotting time does not significantly deviate from that expected for the individual components. At higher concentrations (greater than 0.3 units heparin/ml plus 1.5 μg LACI/ml), the clotting time increasingly deviates from those expected from the individual components and the potentiation effect becomes apparent. For example, 0.5 units heparin/ml plus 2.5 μg LACI/ml has a PT of ~1,000 sec. while 1 unit heparin/ml or 5 μg LACI/ml have PTs of less than 200 sec.

Figure 4B:
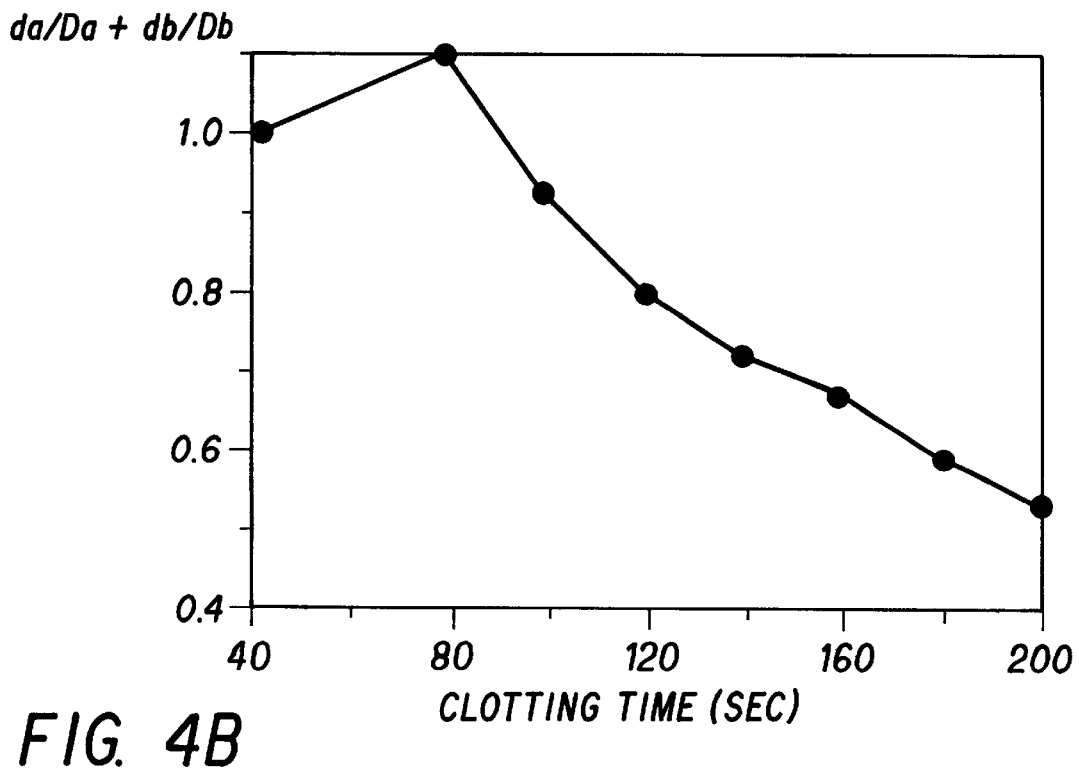

Pharmacologically, drug interactions can be analyzed by the isobole (isoeffective curve) method using the interaction index as a criteria to differentiate zero interaction, synergism, or antagonism (18). The drug interaction index is defined as da/Da+db/Db, where da and db are concentrations of A and B in the combination, respectively, and Da and Db are the concentrations of A and B separately that are isoeffective with the combination. The value of the interaction index reflects the type of interaction: a value of=1 suggests zero interaction; a value of <1 indicates synergism; and a value of>1 shows antagonism. Based on the data of FIG. 4(A), iso-effective concentrations of the compounds (i.e. LACI, heparin separately and their combinations that give the same clotting times) can be obtained for the calculation of the interaction indexes. FIG. 4(B) shows the interaction index as a function of clotting time. The result clearly shows an increasing synergy or potentiation (interaction index <1) with increasing clotting time due to the combined use of increasing concentration of LACI and heparin.

Heparin Enhances the Inhibition of TF-induced Clotting by LACI

In order to estimate the relative potency of LACI in the absence and the presence of heparin, a LACI-depleted plasma was supplemented with various concentrations of LACI and heparin and their PTs were determined. FIG. 5 shows the PT as a function of the concentration of LACI in the absence of heparin (x), in the presence of 0.5 (●), 1.0 (▲), and 2.0 (Δ) units heparin/ml plasma, respectively. If it is assumed that the slope reflects the potency, then the relative potency of LACI increases 3.4, 8.5, and 75 fold in the presence of 0.5, 1.0, and 2.0 units heparin/ml plasma, respectively, over that in the absence of exogenously added heparin.

Effect of Sulfated Polysaccharides and their Combination with LACI on the PT of Plasma In view of the ability of heparin to inhibit TF-induced clotting in a LACI-dependent and independent manner, other sulfated polysaccharides were also tested for their anticoagulant effect. FIG. 6 shows the effect of various sulfated polysaccharides on the PT of normal plasma. All the compounds tested exhibited the ability to prolong the clotting time but this effect was observed at very different concentrations. By weight, the relative potencies of these compounds are in the following order: low molecular weight heparin (mean $M_r$=5100)>unfractionated heparin>low molecular weight heparin (mean $M_r=^{3700}$)>pentosan polysulfate>dermatan sulfate>dextran sulfate>heparan sulfate. To examine whether these compounds also potentiated the LACI-dependent anticlotting activity, tests similar to that described in FIG. 4(A) were carried out. FIGS. 7(A)–(F) shows the effect of LACI, sulfated polysaccharides, and their combinations on the PT of normal plasma. All the compounds tested potentiated the inhibition of TF-induced clotting by LACI, but at very different concentrations. The concentrations of the sulfated polysaccharides that potentiated the LACI anticlotting ativity were in a similar range as those used in FIG. 6 and the relative potencies are by weight in the same order as above.

TABLE 1

Effect of anti-LACI-Ig on the prothrombin time of a normal plasma.

| TF dilution[b] | prothrombin time (sec)[a] | |
|---|---|---|
| | plasma + normal rabbit Ig[c] | plasma + anti-LACI-Ig[d] |
| 1:10 | 27.1 | 25.5 |
| 1:100 | 44.6 | 42.7 |

TABLE 1-continued

Effect of anti-LACI-Ig on the prothrombin time of a normal plasma.

| | prothrombin time (sec)[a] | |
| --- | --- | --- |
| TF dilution[b] | plasma + normal rabbit Ig[c] | plasma + anti-LACI-Ig[d] |
| 1:1,000 | 86.1 | 75.5 |
| 1:10,000 | 175.7 | 129.1 |

[a]Prothrombin time was assayed as described in METHODS. The values are averages of two determinations.
[b]TF was serially diluted into a saline solution containing 1 mg/ml bovine serum albumin.
[c]A normal plasma (1.95 ml) was mixed with 0.5 ml of normal rabbit Ig (1.6 mg/ml) and incubated at 4° for 3 h. before the assay.
[d]Same as in c. except that anti-LACI-Ig was used instead of normal rabbit Ig.

The anticoagulant combination of LACI and sulfated polysaccharide can be used to inhibit both the intrinsic and extrinsic pathways of coagulation by suitable administration to a warm blooded mammal in need of such treatment such as, for example, as may be needed for disseminated intravascular coagulation. The amount of the combination which would normally be administered is primarily dependent upon the physical characteristics of the mammal and the severity of the pathological condition. The amount must be an effective amount, that is, an amount which is medically beneficial for inhibiting coagulation but which does not present toxic effects which overweigh the advantages which accompany its use. The preferable route of administration is oral or parenteral. Administration of the combination in solution with conventional diluents and carriers, for example, physiologic saline, is illustrative. Other suitable formulations of the active combination in pharmaceutically acceptable diluents or carriers in therapeutic dosage can be prepared by reference to general texts in the field such as, for example, *Remington's Pharmaceutical Sciences*, Eighteenth Edition, 1990, Mack Publishing Co., Easton, Pa.

A preferred administration and dosage is parenteral administration of a synergistic combination which is essentially free from antithrombin and consists essentially of from about 0.1 to about 4 units of heparin and about 0.1 $\mu$g to about 5 $\mu$g of LACI per ml of plasma in the whole blood of the recipient. Although antithrombin is essentially absent in the combination of LACI and heparin that is thus exogenously administered, it will be understood that the whole blood of the recipient will contain a substantial level of the naturally-occurring coagulation inhibitor, antithrombin.

For example, in Chapter 53 by P. C. Harpel in the well-known text: *Hemostasis and Thrombosis. Basic Principles and Clinical Practice*, R. W. Colman et al., Eds., J. B. Lippincott, Philadelphia, 1982, it is stated at page 739 that the plasma concentration of antithrombin ranges from 18 to 30 mg/dl (3–5 $\mu$M).

Various other examples will be apparent to the person skilled in the art after reading the present disclosure without departing from the spirit and scope of the invention. It is intended that all such other examples be included within the scope of the appended claims.

REFERENCES

1. Rosenberg, R. D. (1977) Fed. Proc. 36, 10–18.
2. Holmer, E., Kurachi K., and Soderstrom, G. (1981) Biochem. J. 193, 395–400.
3. Casu, B. (1985) Adv. Carbohydr. Chem. Biochem. 43, 51–134.
4. Ofosu, F. A., Buchanan, M. R., Anvari, N., Smith, L. M., and Blajchman, M. A. (1989) Ann. N. Y. Acad. Sci. 556, 123–131.
5. Godal, H. C., Rygh, M., and Laake, K. (1974) Thromb. Res. 5, 773–775.
6. Jesty, J. (1978) Arch. Biochem. Biophys. 185, 165–175.
7. Broze, G. J. Jr., and Majerus, P. W. (1980) J. Biol. Chem. 255, 1242–1247.
8. Kondo, S. and Kisiel, W. (1987) Thromb. Res. 46, 325–335.
9. Nemerson, Y. (1988) Blood 71,1–8.
10. Walker, F. J. and Esmon, C. T. (1979) Biochim. Biophys. Acta 585, 405–415.
11. Ofosu, F. A., Modi, G., Cersku, A. L., Hirsh, J., and Blajchman, M. A. (1982) Thromb. Res. 28, 487–497.
12. Broze, G. J. Jr., Warren, L. A., Novotny, W. F., Higuchi, D. A., Girard, J. J., and Miletich, J. P. (1988) Blood 71, 335–343.
13. Rao, L. V. M. and Rapaport, S. I. (1987) Blood 69, 645–651.
14. Broze, G. J. Jr. and Miletich, J. P. (1987) Proc. Natl. Acad. Sci. U.S.A. 84, 1886–1890.
15 Wun T-C., Kretzmer, K. K., Girard, T. J., Miletich, J. P., and Broze, G. J. Jr. (1988) J. Biol. Chem. 263, 6001–6004.
16. Chase, T. Jr., and Shaw, E. (1970) Methods Emzymol. 19, 20–27.
17. Ishii, S-h., Yokosawa, H., Kumazaki, T., and Nakamura, I. (1983) Methods Enzymol. 91, 378–383.
18. Berenbaum, M. C. (1989) Pharmacol. Rev. 41, 93–141.

What is claimed is:

1. A composition essentially free from antithrombin and consisting essentially of LACI and an anticoagulant sulfated polysaccharide in proportions that provide a synergistic anticoagulation effect upon administration to a warm-blooded mammal.

2. A composition of claim 1 in which the sulfated polysaccharide is selected from the group consisting of heparin, pentosan sulfate, dermatan sulfate, dextran sulfate and heparan sulfate.

3. A composition according to claim 1 in which heparin and LACI are in proportions of from about 0.1 to about 4 units of said heparin and from about 0.1 to about 5 $\mu$g of LACI.

4. A method of inhibiting blood coagulation in whole blood plasma of a warm blooded mammal comprising exogenously administering to said mammal an effective synergistic anticoagulant amount of an anticoagulant sulfated polysaccharide and LACI essentially free from antithrombin.

5. The method of claim 4 in which the sulfated polysaccharide is selected from the group consisting of heparin, pentosan sulfate, dermatan sulfate, dextran sulfate and heparan sulfate.

6. The method of claim 4 in which the administration is parenterally in an amount of from 0.1 to about 4 units of heparin and from about 0.1 to about 5 $\mu$g of LACI per ml of plasma treated.

* * * * *